United States Patent
Iaccino et al.

(10) Patent No.: US 10,294,175 B2
(45) Date of Patent: *May 21, 2019

(54) PROCESS FOR CONVERSION OF ACYCLIC $C_5$ COMPOUNDS TO CYCLIC $C_5$ COMPOUNDS AND CATALYST COMPOSITION FOR USE THEREIN

(71) Applicant: ExxonMobil Chemical Patents Inc., Baytown, TX (US)

(72) Inventors: Larry L. Iaccino, Seabrook, TX (US); Jeremy W. Bedard, Houston, TX (US); Karl G. Strohmaier, Port Murray, NJ (US); Machteld M. W. Mertens, Boortmeerbeek (BE); Robert T. Carr, High Bridge, NJ (US); Jane C. Cheng, Bethlehem, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 33 days.

This patent is subject to a terminal disclaimer.

(21) Appl. No.: 15/288,364

(22) Filed: Oct. 7, 2016

(65) Prior Publication Data

US 2017/0121245 A1   May 4, 2017

Related U.S. Application Data

(60) Provisional application No. 62/250,681, filed on Nov. 4, 2015.

(51) Int. Cl.
| | |
|---|---|
| *C07C 5/327* | (2006.01) |
| *C07C 5/32* | (2006.01) |
| *C07C 5/333* | (2006.01) |
| *C07C 5/373* | (2006.01) |
| *B01J 29/46* | (2006.01) |
| *B01J 29/44* | (2006.01) |
| *B01J 29/62* | (2006.01) |
| *C07C 5/42* | (2006.01) |

(52) U.S. Cl.
CPC ............... *C07C 5/373* (2013.01); *B01J 29/44* (2013.01); *B01J 29/46* (2013.01); *B01J 29/62* (2013.01); *C07C 5/42* (2013.01); *C07C 2529/44* (2013.01); *C07C 2529/46* (2013.01); *C07C 2529/62* (2013.01); *C07C 2601/06* (2017.05); *C07C 2601/10* (2017.05)

(58) Field of Classification Search
CPC ............ C07C 5/327; C07C 5/32; C07C 5/333
USPC ........................................ 585/365, 366, 369
See application file for complete search history.

(56) References Cited

U.S. PATENT DOCUMENTS

| | | | |
|---|---|---|---|
| 2,438,398 A | 3/1948 | Kennedy et al. | |
| 2,438,399 A | 3/1948 | Kennedy et al. | |
| 2,438,400 A | 3/1948 | Hetzel et al. | |
| 2,438,401 A | 3/1948 | Kennedy et al. | |
| 2,438,402 A | 3/1948 | Kennedy et al. | |
| 2,438,403 A | 3/1948 | Kennedy et al. | |
| 2,438,404 A | 3/1948 | Hetzel et al. | |
| 3,631,209 A | 12/1971 | Frech et al. | |
| 3,953,368 A | 4/1976 | Sinfelt | |
| 4,246,202 A | 1/1981 | Cihonski | |
| 4,886,926 A | 12/1989 | Dessau et al. | |
| 4,927,525 A | 5/1990 | Chu | |
| 5,192,728 A | 3/1993 | Dessau et al. | |
| 5,254,787 A | 10/1993 | Dessau | |
| 5,283,385 A | 2/1994 | Dessau | |
| 5,284,986 A | 2/1994 | Dessau | |
| 2009/0062446 A1 | 3/2009 | Wei et al. | |
| 2013/0153456 A1 | 6/2013 | Zhu et al. | |

FOREIGN PATENT DOCUMENTS

| | | |
|---|---|---|
| DE | 253809 | 3/1976 |
| DE | 2535809 | 3/1976 |
| WO | WO 89/04818 | 6/1989 |
| WO | 2013/176712 | 11/2013 |

OTHER PUBLICATIONS

U.S. Appl. No. 62/250,675, filed Nov. 4, 2015, Iaccino et al.
U.S. Appl. No. 62/250,681, filed Nov. 4, 2015, Iaccino et al.
U.S. Appl. No. 62/250,688, filed Nov. 4, 2015, Iaccino et al.
U.S. Appl. No. 62/250,689, filed Nov. 4, 2015, Iaccino et al.
Bricker, J.C., et al., "Advanced Catalytic Dehydrogenation Technologies for Production of Olefins," Topics in Catalysis, 2012, vol. 55, Issue 19-20, pp. 1309-1314.
Fel'dblyum, V.S., et al. "Cyclization and Dehydrocyclization of $C_5$ Hydrocarbons over Platinum Nanocatalysts and in the Presence of Hydrogen Sulfide," Doklady Chemistry, 2009, vol. 424, Part 2, pp. 27-30.
Kanazirev, V., et al. "Conversion of $C_8$ Aromatics and n-Pentane Over $Ga_2O_3$/HZSM-5 Mechanically Mixed Catalysts", Catalysis Letters, 1991, vol. 9, pp. 35-42.
Kennedy, R.M. et al., "Formation of Cyclopentadiene from 1,3-Pentadiene," Industrial and Engineering Chemistry, 1950, vol. 42, No. 3, pp. 547-552.
Li, X., et al. "Catalytic Dehydroisomerization of n-alkanes to Isoalkenes," Journal of Catalysis, 2008, vol. 255, pp. 134-137.
Lopez, C.M., et al. "n-Pentane Hydroisomerization on Pt Containing HZSM-5, HBEA and SAPO-11," Catalysis Letters, 2008, vol. 122, pp. 267-273.

(Continued)

Primary Examiner — Thuan D Dang

(57) ABSTRACT

Disclosed is a process for the conversion of acyclic $C_5$ feedstock to a product comprising cyclic $C_5$ compounds, such as for example, cyclopentadiene, and catalyst compositions for use in such process. The process comprising the steps of contacting said feedstock and, optionally, hydrogen under acyclic $C_5$ conversion conditions in the presence of a catalyst composition to form said product. The catalyst composition comprising a crystalline aluminosilicate having a constraint index of less than or equal to 5, and a Group 10 metal, and, optionally, a Group 11 metal, in combination with a Group 1 alkali metal and/or a Group 2 alkaline earth metal.

18 Claims, No Drawings

(56) References Cited

OTHER PUBLICATIONS

Marcinkowski, T.E., "*Isomerization and Dehydrocyclization of 1,3-Pentadiene*," Retrospective Theses and Dissertations, 1979, Paper 433, pp. 1-110.
Trakarnroek, et al., "*Effect of Zeolite Crystallite Size on Pt/KL Catalysts Used for the Aromatization of n-Octane*", Chemical Engineering Communications, vol. 194, No. 7, Apr. 2, 2007, pp. 946-961.
Vaarkamp, et al., "*Sulfur Poisoning of a Pt/BaK-LTL Catalyst: A Catalytic and Structural Study Using Hydrogen Chemisorption and X-ray Absorption Spectroscopy*," Journal of Catalysis, vol. 138, No. 2, Dec. 1992, pp. 675-685.
Vora, B.V., "*Development of Dehydrogenation Catalysts and Processes*," Topics in Catalysis, 2012, vol. 55, pp. 1297-1308.
Xinghua, Z., et al. "*Aqueous-Phase Catalytic Process for Production of Pentane from Furfural Over Nickel-Based Catalysts*," Fuel, 2010, vol. 89, pp. 2697-2702.
Xu, Y., "*Methane activation without using oxidants over Mo/HZSM-5 zeolite catalysts*," Catalysis Letters, 1995, vol. 30, pp. 135-149.

PROCESS FOR CONVERSION OF ACYCLIC $C_5$ COMPOUNDS TO CYCLIC $C_5$ COMPOUNDS AND CATALYST COMPOSITION FOR USE THEREIN

CROSS-REFERENCE TO RELATED APPLICATIONS

This invention claims priority to and the benefit of U.S. Ser. No. 62/250,681, filed Nov. 4, 2015. This application relates to U.S. Ser. No. 62/250,675, filed Nov. 4, 2015, U.S. Ser. No. 62/250,688, filed Nov. 4, 2015, and U.S. Ser. No. 62/250,689, filed Nov. 4, 2015.

FIELD OF THE INVENTION

This invention relates to a process for the conversion of acyclic $C_5$ feedstock to a product comprising cyclic $C_5$ compounds, such as for example, cyclopentadiene, and catalyst compositions for use in such process.

BACKGROUND OF THE INVENTION

Cyclopentadiene (CPD) and its dimer dicyclopentadiene (DCPD) are highly desired raw materials used throughout the chemical industry in a wide range of products such as polymeric materials, polyester resins, synthetic rubbers, solvents, fuels, fuel additives, etc. In addition, cyclopentane and cyclopentene are useful as solvents, and cyclopentene may be used as a monomer to produce polymers and as a starting material for other high value chemicals.

Cyclopentadiene (CPD) is currently a minor byproduct of liquid fed steam cracking (for example, naphtha and heavier feed). As existing and new steam cracking facilities shift to lighter feeds, less CPD is produced while demand for CPD is rising. High cost due to supply limitations impacts the potential end product use of CPD in polymers. More CPD-based polymer products and other high value products could be produced, if additional CPD could be produced, at unconstrained rates and preferably at a cost lower than recovery from steam cracking. Cyclopentane and cyclopentene also have high value as solvents while cyclopentene may be used as a co-monomer to produce polymers and as a starting material for other high value chemicals.

It would be advantageous to be able to produce cyclic $C_5$ compounds including CPD as the primary product from plentiful $C_5$ feedstock using a catalyst system to produce CPD while minimizing production of light ($C_{4-}$) byproducts. While lower hydrogen content feedstock (for example, cyclics, alkenes, dialkenes) could be preferred because the reaction endotherm is reduced and thermodynamic constraints on conversion are improved, non-saturates are more expensive than saturate feedstock. Linear $C_5$ skeletal structure is preferred over branched $C_5$ skeletal structures due to both reaction chemistry and the lower value of linear $C_5$ relative to branched $C_5$ (due to octane differences). An abundance of $C_5$ is available from unconventional gas and shale oil as well as reduced use in motor fuels due to stringent fuel regulations. $C_5$ feedstock may also be derived from bio-feeds.

Dehydrogenation technologies are currently used to produce mono-olefins and di-olefins from $C_3$ and $C_4$ alkanes, but not cyclic mono-olefins or cyclic di-olefins. A typical process uses Pt/Sn supported on alumina as the active catalyst. Another useful process uses chromia on alumina. See, B. V. Vora, "Development of Dehydrogenation Catalysts and Processes", Topics in Catalysis, vol. 55, pp. 1297-1308, 2012; and J. C. Bricker, "Advanced Catalytic Dehydrogenation Technologies for Production of Olefins", Topics in Catalysis, vol. 55, pp. 1309-1314, 2012.

Still another common process uses Pt/Sn supported on Zn and/or Ca aluminate to dehydrogenate propane. While these processes are successful in dehydrogenating alkanes, they do not perform cyclization which is critical to producing CPD. Pt—Sn/alumina and Pt—Sn/aluminate catalysts exhibit moderate conversion of n-pentane, but such catalyst have poor selectivity and yield to cyclic $C_5$ products.

Pt supported on chlorided alumina catalysts are used to reform low octane naphtha to aromatics such as benzene and toluene. See, U.S. Pat. No. 3,953,368 (Sinfelt), "Polymetallic Cluster Compositions Useful as Hydrocarbon Conversion Catalysts." While these catalysts are effective in dehydrogenating and cyclizing $C_6$ and higher alkanes to form $C_6$ aromatic rings, they are less effective in converting acyclic $C_5$s to cyclic $C_5$s. These Pt on chlorided alumina catalysts exhibit low yields of cyclic $C_5$ and exhibit deactivation within the first two hours of time on stream. Cyclization of $C_6$ and $C_7$ alkanes is aided by the formation of an aromatic ring, which does not occur in $C_5$ cyclization. This effect may be due in part to the much higher heat of formation for CPD, a cyclic $C_5$, as compared to benzene, a cyclic $C_6$, and toluene, a cyclic $C_7$. This is also exhibited by Pt/Ir and Pt/Sn supported on chlorided alumina. Although these alumina catalysts perform both dehydrogenation and cyclization of $C_{6+}$ species to form $C_6$ aromatic rings, a different catalyst will be needed to convert acyclic $C_5$ to cyclic $C_5$.

Ga-containing ZSM-5 catalysts are used in a process to produce aromatics from light paraffins. A study by Kanazirev et al., showed n-pentane is readily converted over $Ga_2O_3$/H-ZSM-5. See Kanazirev et al., "Conversion of $C_8$ aromatics and n-pentane over $Ga_2O_3$/H-ZSM-5 mechanically mixed catalysts," Catalysis Letters, vol. 9, pp. 35-42, 1991. No production of cyclic $C_5$ was reported while upwards of 6 wt % aromatics were produced at 440° C. and 1.8 $hr^{-1}$ WHSV. Mo/ZSM-5 catalysts have also been shown to dehydrogenate and/or cyclize paraffins, especially methane. See, Y. Xu, S. Liu, X. Guo, L. Wang, and M. Xie, "Methane activation without using oxidants over Mo/HZSM-5 zeolite catalysts," Catalysis Letters, vol. 30, pp. 135-149, 1994. High conversion of n-pentane using Mo/ZSM-5 was demonstrated with no production of cyclic $C_5$ and high yield to cracking products. This shows that ZSM-5-based catalysts can convert paraffins to a $C_6$ ring, but not necessarily to produce a $C_5$ ring.

U.S. Pat. No. 5,254,787 (Dessau) introduced the NU-87 catalyst used in the dehydrogenation of paraffins. This catalyst was shown to dehydrogenate $C_{2-5}$ and $C_{6+}$ to produce their unsaturated analogs. A distinction between $C_{2-5}$ and $C_{6+}$ alkanes was made explicit in this patent: dehydrogenation of $C_{2-5}$ alkanes produced linear or branched mono-olefins or di-olefins whereas dehydrogenation of $C_{6+}$ alkanes yielded aromatics. U.S. Pat. No. 5,192,728 (Dessau) involves similar chemistry, but with a tin-containing crystalline microporous material. As with the NU-87 catalyst, $C_5$ dehydrogenation was only shown to produce linear or branched, mono-olefins or di-olefins and not CPD.

U.S. Pat. No. 5,284,986 (Dessau) introduced a dual-stage process for the production of cyclopentane and cyclopentene from n-pentane. An example was conducted wherein the first stage involved dehydrogenation and dehydrocyclization of n-pentane to a mix of paraffins, mono-olefins and di-olefins, and naphthenes over a Pt/Sn-ZSM-5 catalyst. This mixture was then introduced to a second-stage reactor consisting of Pd/Sn-ZSM-5 catalyst where dienes, especially CPD, were converted to olefins and saturates. Cyclopentene was were the desired product in this process, whereas CPD was an unwanted byproduct.

U.S. Pat. Nos. 2,438,398; 2,438,399; 2,438,400; 2,438,401; 2,438,402; 2,438,403, and 2,438,404 (Kennedy) disclosed production of CPD from 1,3-pentadiene over various catalysts. Low operating pressures, low per pass conversion, and low selectivity make this process undesirable. Additionally, 1,3-pentadiene is not a readily available feedstock, unlike n-pentane. See also, Kennedy et al., "Formation of Cyclopentadiene from 1,3-Pentadiene," Industrial & Engineering Chemistry, vol. 42, pp. 547-552, 1950.

Fel'dblyum et al. in "Cyclization and dehydrocyclization of $C_5$ hydrocarbons over platinum nanocatalysts and in the presence of hydrogen sulfide," *Doklady Chemistry*, vol. 424, pp. 27-30, 2009, reported production of CPD from 1,3-pentadiene, n-pentene, and n-pentane. Yields to CPD were as high as 53%, 35%, and 21% for the conversion of 1,3-pentadiene, n-pentene, and n-pentane respectively at 600° C. on 2% $Pt/SiO_2$. While initial production of CPD was observed, drastic catalyst deactivation within the first minutes of the reaction was observed. Experiments conducted on Pt-containing silica show moderate conversion of n-pentane over Pt—$Sn/SiO_2$, but with poor selectivity and yield to cyclic $C_5$ products. The use of $H_2S$ as a 1,3-pentadiene cyclization promoter was presented by Fel'dblyum, infra, as well as in Marcinkowski, "Isomerization and Dehydrogenation of 1,3-Pentadiene," M.S., University of Central Florida, 1977. Marcinkowski showed 80% conversion of 1,3,-pentadiene with 80% selectivity to CPD with $H_2S$ at 700° C. High temperature, limited feedstock, and potential of products containing sulfur that would later need scrubbing make this process undesirable.

López et al. in "n-Pentane Hydroisomerization on Pt Containing HZSM-5, HBEA and SAPO-11," *Catalysis Letters*, vol. 122, pp. 267-273, 2008, studied reactions of n-pentane on Pt-containing zeolites including H-ZSM-5. At intermediate temperatures (250-400° C.), they reported efficient hydroisomerization of n-pentane on the Pt-zeolites with no discussion of cyclopentenes formation. It is desirable to avoid this deleterious chemistry as branched $C_5$ do not produce cyclic $C_5$ as efficiently as linear $C_5$, as discussed above.

Li et al. in "Catalytic dehydroisomerization of n-alkanes to isoalkenes," *Journal of Catalysis*, vol. 255, pp. 134-137, 2008, also studied n-pentane dehydrogenation on Pt-containing zeolites in which Al had been isomorphically substituted with Fe. These Pt/[Fe]ZSM-5 catalysts were efficient dehydrogenating and isomerizing n-pentane, but under the reaction conditions used, no cyclic $C_5$ were produced and undesirable skeletal isomerization occurred.

In view of this state of the art, there remains a need for a process to convert acyclic $C_5$ feedstock to non-aromatic, cyclic $C_5$ hydrocarbon, namely CPD, preferably at commercial rates and conditions. Further, there is a need for a catalytic process targeted for the production of cyclopentadiene which generates cyclopentadiene in high yield from plentiful $C_5$ feedstocks without excessive production of $C_{4-}$ cracked products and with acceptable catalyst aging properties. This invention meets this and other needs.

SUMMARY OF THE INVENTION

In a first aspect, the invention relates to a process for conversion of an acyclic $C_5$ feedstock to a product comprising cyclic $C_5$ compounds, particularly CPD. This process, comprises the steps of contacting said feedstock and, optionally, hydrogen under acyclic $C_5$ conversion conditions in the presence of a catalyst composition of this invention to form said product.

In a second aspect, the invention relates to a catalyst composition for use in the acyclic $C_5$ conversion process. This catalyst composition comprising a microporous crystalline aluminosilicate having a constraint index of less than or equal to 5, and a Group 10 metal, and, optionally, a Group 11 metal in combination with a Group 1 alkali metal and/or a Group 2 alkaline earth metal. The microporous crystalline aluminosilicate which has a constraint index in the range of less than or equal to 5 preferably is selected from the group consisting of zeolite beta, mordenite, faujasite, zeolite L, and mixtures of two or more thereof. The Group 10 metal is preferably, platinum, and more preferably in the amount of at least 0.005 wt %, based on the weight of the catalyst composition. The Group 11 metal is preferably copper or silver. The Group 1 alkali metal is preferably potassium.

The crystalline aluminosilicate has a $SiO_2/Al_2O_3$ molar ratio of at least 2, preferably in the range of from about 2 up to about 20.

The catalyst composition has a BET surface area of at least 275 $m^2/g$, or in the range of about greater than about 275 $m^2/g$ to less than about 400 $m^2/g$.

The Group 11 metal content of said catalyst composition is at least 0.01 molar ratio to the Group 10 metal, based on the molar quantities of each in the catalyst composition.

The molar ratio of the sum of said Group 1 alkali metal and Group 2 alkaline earth metal to Al is at least 0.5.

The catalyst composition provides (i) a conversion of at least 20% of said acyclic $C_5$ feedstock and/or (ii) a carbon selectivity to cyclic $C_5$ compounds of at least about 20% under acyclic $C_5$ conversion conditions including an n-pentane feedstock with equimolar $H_2$, a temperature of about 450° C., an n-pentane partial pressure of about 5 psia (35 kPa-a), and an n-pentane weight hourly space velocity of about 2 $hr^{-1}$.

In a third aspect, the invention relates to a method of making the catalyst composition. The method of making the catalyst composition comprising the steps of:
(a) providing a crystalline aluminosilicate comprising a Group 1 alkali metal and/or a Group 2 alkaline earth metal and having a constraint index of less than or equal to 5;
(b) optionally, treating said crystalline aluminosilicate with an acid at a PH of greater than or equal to 7 to increase the surface area of said crystalline aluminosilicate and to form an acid-treated aluminosilicate; and
(c) contacting said acid-treated aluminosilicate of step (b) with a source of a Group 10 metal, and/or optionally said Group 11 metal, to form said catalyst composition, whereby said catalyst composition having said Group 10 metal, and/or optionally said Group 11 metal, deposited thereon.

In a fourth aspect, the invention relates to a catalyst composition made by any one of the methods of this invention.

DETAILED DESCRIPTION OF THE INVENTION

Definitions

For the purpose of this specification and appended claims, the following terms are defined.

The term "saturates" includes, but is not limited to, alkanes and cycloalkanes.

The term "non-saturates" includes, but is not limited to, alkenes, dialkenes, alkynes, cyclo-alkenes, and cyclo-dialkenes.

The term "cyclic $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclic" includes, but is not limited to, linear and branched saturates and non-saturates.

The term "aromatic" means a planar cyclic hydrocarbyl with conjugated double bonds, such as, for example, benzene. As used herein, the term aromatic encompasses compounds containing one or more aromatic rings, including, but not limited to, benzene, toluene and xylene and polynuclear aromatics (PNAs) which include naphthalene, anthracene, chrysene, and their alkylated versions. The term "$C_{6+}$ aromatics" includes compounds based upon an aromatic ring having six or more ring atoms, including, but not limited to, benzene, toluene and xylene and polynuclear aromatics (PNAs) which include naphthalene, anthracene, chrysene, and their alkylated versions.

The term "BTX" includes, but is not limited to, a mixture of benzene, toluene and xylene (ortho and/or meta and/or para).

The term "coke" includes, but is not limited to, a low hydrogen content hydrocarbon that is adsorbed on the catalyst composition.

The term "$C_n$" means hydrocarbon(s) having n carbon atom(s) per molecule, wherein n is a positive integer.

The term "$C_{n+}$" means hydrocarbon(s) having at least n carbon atom(s) per molecule.

The term "$C_{n-}$" means hydrocarbon(s) having no more than n carbon atom(s) per molecule.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "$C_5$ feedstock" includes a feedstock containing n-pentane, such as, for example, a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27, (1985), unless otherwise specified.

The term "Group 10 metal" means an element in Group 10 of the Periodic Table and includes, but is not limited to, nickel, palladium, and platinum.

The term "Group 11 metal" means an element in Group 11 of the Periodic Table and includes, but is not limited to, copper, silver, gold, and a mixture of two or more thereof.

The term "Group 1 alkali metal" means an element in Group 1 of the Periodic Table and includes, but is not limited to, lithium, sodium, potassium, rubidium, cesium, and a mixture of two or more thereof, and excludes hydrogen.

The term "Group 2 alkaline earth metal" means an element in Group 2 of the Periodic Table and includes, but is not limited to, beryllium, magnesium, calcium, strontium, barium, and a mixture of two or more thereof.

The term "constraint index" is defined in U.S. Pat. Nos. 3,972,832 and 4,016,218, both of which are incorporated herein by reference.

As used herein, the term "molecular sieve" is used synonymously with the term "microporous crystalline material" and zeolite.

As used herein, the term "carbon selectivity" means the moles of carbon in the respective cyclic $C_5$, CPD, $C_1$, and $C_{2-4}$ formed divided by total moles of carbon in the pentane converted. The phrase "a carbon selectivity to cyclic $C_5$ of at least 20%" means that at least 20 moles of carbon in the cyclic $C_5$ is formed per 100 moles of carbon in the pentane converted.

As used herein, the term "conversion" means the moles of carbon in the acyclic $C_5$ feedstock that is converted to a product. The phrase "a conversion of at least 20% of said acyclic $C_5$ feedstock to said product" means that at least 20% of the moles of said acyclic $C_5$ feedstock was converted to a product.

As used herein, the term "reactor system" refers to a system including one or more reactors and all optional equipment used in the production of cyclopentadiene.

As used herein, the term "reactor" refers to any vessel(s) in which a chemical reaction occurs. Reactor includes both distinct reactors as well as reaction zones within a single reactor apparatus and as applicable, reactions zones across multiple reactors. For example, a single reactor may have multiple reaction zones. Where the description refers to a first and second reactor, the person of ordinary skill in the art will readily recognize such reference includes two reactors, as well as a single reactor vessel having first and second reaction zones. Likewise, a first reactor effluent and a second reactor effluent will be recognized to include the effluent from the first reaction zone and the second reaction zone of a single reactor, respectively.

A reactor/reaction zone may be an adiabatic reactor/reaction zone or a diabatic reactor/reaction zone. As used herein the term "adiabatic" refers to a reaction zone for which there is essentially no heat input into the system other than by a flowing process fluid. A reaction zone that has unavoidable losses due to conduction and/or radiation may also be considered adiabatic for the purpose of this invention. As used herein the term "diabatic" refers to a reactor/reaction zone to which heat is supplied by a means in addition to that provided by the flowing process fluid.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where Umf is minimum fluidizing velocity, Umb is minimum bubbling velocity, Uc is the velocity at which fluctuation in pressure peaks, and tr is transport velocity. These different fluidization regimes have been described in, for example, Kunii, D., Levenspiel, O., Chapter 3 of *Fluidization Engineering*, 2$^{nd}$ Edition, Butterworth-Heinemann, Boston, 1991 and Walas, S. M., Chapter 6 of *Chemical Process Equipment*, Revised 2$^{nd}$ Edition, Butterworth-Heinemann, Boston, 2010, which are incorporated by reference.

As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), U<$U_{mf}$ in at least a portion of the reaction zone, and/or operating at a velocity higher than the minimum fluidization velocity while maintaining a gradient in gas and/or solid property (such as, temperature, gas or solid composition, etc.) axially up the reactor bed by using reactor internals to minimize gas-solid back-mixing. Description of the minimum fluidization velocity is given in, for example, Kunii, D., Levenspiel, O., Chapter 3 of *Fluidization Engineering*, 2$^{nd}$ Edition, Butterworth-Heinemann, Boston, 1991 and Walas, S. M., Chapter 6 of *Chemical Process Equipment*, Revised 2$^{nd}$ Edition, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. As used herein, the term "cascaded fluid-beds" means a series arrangement of individual fluid-beds such that there can be a gradient in gas and/or solid property (such as, temperature, gas or solid composition, pressure, etc.) as the solid or gas cascades from one fluid-bed to another. Locus of minimum fluidization velocity is given in, for example, Kunii, D., Levenspiel, O., Chapter 3 of *Fluidization Engineering*, 2$^{nd}$ Edition, Butterworth-Heinemann, Boston, 1991 and Walas, S. M., Chapter 6 of *Chemical Process Equipment*, Revised 2$^{nd}$ Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated and/or separated from the product stream and then returned back to the reactor.

As used herein, the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, 2$^{nd}$ Edition, Butterworth-Heinemann, Boston, 1991 and Walas, S. M., Chapter 6 of *Chemical Process Equipment*, Revised 2$^{nd}$ Edition, Butterworth-Heinemann, Boston, 2010. A fluidized bed reactor, such as a circulating fluidized bed reactor, may be operated as a riser reactor.

As used herein, the term "fired tubes" reactor refers to a furnace and parallel reactor tube(s) positioned within a radiant section of the furnace. The reactor tubes contain a catalytic material (e.g., catalyst particles), which contacts reactant(s) to form a product.

As used herein, the term "convectively heated tubes" reactor refers to a conversion system comprising parallel reactor tube(s) containing a catalytic material and positioned within an enclosure. While any known reactor tube configuration or enclosure may be used, preferably the conversion system comprises multiple parallel reactor tubes within a convective heat transfer enclosure. Preferably, the reactor tubes are straight rather than having a coiled or curved path through the enclosure (although coiled or curved tubes may be used). Additionally, the tubes may have a cross section that is circular, elliptical, rectangular, and/or other known shapes. The tubes are preferentially heated with a turbine exhaust stream produced by a turbine burning fuel gas with a compressed gas comprising oxygen. In other aspects, the reactor tubes are heated by convection with hot gas produced by combustion in a furnace, boiler, or excess air burner. However, heating the reactor tubes with turbine exhaust is preferred because of the co-production of shaft power among other advantages.

As used herein, the term "fixed bed" or "packed bed" reactor refers to a zone or vessel (such as, vertical or horizontal, cylindrical pipe or a spherical vessel) and may include transverse (also known as cross flow), axial flow and/or radial flow of the gas, where solids (e.g., catalyst particles) are substantially immobilized within the reactor and gas flows such that the superficial velocity (U) is below the velocity required to fluidize the solid particles (i.e., below the minimum fluidization velocity $U_{mf}$) and/or the gas is moving in a downward direction so that solid particle fluidization is not possible.

As used herein, the term "cyclical" refers to a periodic recurring or repeating event that occurs according to a cycle. For example, reactors (e.g., cyclic fixed bed) may be cyclically operated to have a reaction interval, a reheat interval and/or a regeneration interval. The duration and/or order of the interval steps may change over time.

As used herein, the term "co-current" refers to a flow of two streams (e.g., stream (a), stream (b)) in substantially the same direction. For example, if stream (a) flows from a top portion to a bottom portion of at least one reaction zone and stream (b) flows from a top portion to a bottom portion of at least one reaction zone, the flow of stream (a) would be considered co-current to the flow of stream (b). On a smaller scale within the reaction zone, there may be regions where flow may not be co-current.

As used herein, the term "counter-current" refers to a flow of two streams (e.g., stream (a), stream (b)) in substantially opposing directions. For example, if stream (a) flows from a top portion to a bottom portion of the at least one reaction zone and stream (b) flows from a bottom portion to a top portion of the at least one reaction zone, the flow of stream (a) would be considered counter-current to the flow of stream (b). On a smaller scale within the reaction zone, there may be regions where flow may not be counter-current.

Feedstock

A cyclic $C_5$ feedstock useful herein is obtainable from crude oil or natural gas condensate, and can include cracked $C_5$ (in various degrees of unsaturation: alkenes, dialkenes, alkynes) produced by refining and chemical processes, such as fluid catalytic cracking (FCC), reforming, hydrocracking, hydrotreating, coking, and steam cracking.

The acyclic $C_5$ feedstock useful in the process of this invention comprises pentane, pentene, pentadiene and mixtures of two or more thereof. Preferably, the acyclic $C_5$ feedstock comprises at least about 50 wt %, or 60 wt %, or 75 wt %, or 90 wt % n-pentane, or in the range from about 50 wt % to about 100 wt % n-pentane.

The acyclic $C_5$ feedstock, optionally, does not comprise benzene, toluene, or xylene (ortho, meta, or para), preferably the benzene, toluene, or xylene (ortho, meta, or para) compounds are present at less than 5 wt %, preferably less than 1 wt %, preferably present at less than 0.01 wt %, preferably at 0 wt %.

The acyclic $C_5$ feedstock, optionally, does not comprise $C_{6+}$ aromatic compounds, preferably $C_{6+}$ aromatic compounds are present at less than 5 wt %, preferably less than 1 wt %, preferably present at less than 0.01 wt %, preferably at 0 wt %.

The acyclic $C_5$ feedstock, optionally, does not comprise $C_{4-}$ compounds, any $C_{4-}$ compounds are present at less than 5 wt %, preferably less than 1 wt %, preferably present at less than 0.01 wt %, preferably at 0 wt %.

Acyclic $C_5$ Conversion Process

The first aspect of the invention is a process for conversion of an acyclic $C_5$ feedstock to a product comprising cyclic $C_5$ compounds. The process comprising the steps of contacting said feedstock and, optionally, hydrogen under acyclic $C_5$ conversion conditions in the presence of any one of the catalyst compositions of this invention to form said product. The catalyst composition comprises a microporous crystalline aluminosilicate having a constraint index less than about 5, a Group 10 metal in combination with a Group 1 alkali metal and/or a Group 2 alkaline earth metal and, optionally, a Group 11 metal.

The first aspect of the invention is also a process for conversion of an acyclic $C_5$ feedstock to a product comprising cyclic $C_5$ compounds, the process comprising the steps of contacting said feedstock and, optionally, hydrogen under acyclic $C_5$ conversion conditions in the presence of any one of the catalyst compositions made by any one of the methods of this invention to form said product.

The acyclic $C_5$ conversion process can be conducted in a wide range of reactor configurations including: convectively heated tubes (as described in U.S. Ser. No. 62/250,674, filed Nov. 4, 2015), fired tubes (as described in U.S. Ser. No. 62/250,693, filed Nov. 4, 2015), a riser reactor (as described in U.S. Ser. No. 62/250,682, filed Nov. 4, 2015), a circulating fluidized bed or a circulating settling bed with countercurrent flow (as described in U.S. Ser. No. 62/250,680, filed Nov. 4, 2015), and a cyclic fluidized bed reactor or a cyclic fixed bed reactor (as described in U.S. Ser. No. 62/250,677, filed Nov. 4, 2015). In addition, the $C_5$ conversion process can be conducted in a single reaction zone or in a plurality of reaction zones, such as an adiabatic reaction zone followed by a diabatic reaction zone (as described in U.S. Ser. No. 62/250,697, filed Nov. 4, 2015).

Typically, the acyclic $C_5$ hydrocarbon(s) contained in the $C_5$ feedstock is fed into a first reactor loaded with a catalyst, where the acyclic $C_5$ hydrocarbons contact the catalyst under conversion conditions, whereupon at least a portion of the acyclic $C_5$ hydrocarbon(s) molecules are converted into CPD molecules, and a reaction product containing CPD and, optionally, other cyclic hydrocarbons (e.g., $C_5$ cyclic hydrocarbons such as cyclopentane and cyclopentene) exits the first reactor as a first reactor hydrocarbon effluent. Preferably, a hydrogen co-feedstock comprising hydrogen and, optionally, light hydrocarbons, such as $C_1$-$C_4$ hydrocarbons, is also fed into the first reactor. Preferably, at least a portion of the hydrogen co-feedstock is admixed with the $C_5$ feedstock prior to being fed into the first reactor. The presence of hydrogen in the feed mixture at the inlet location, where the feed first comes into contact with the catalyst, prevents or reduces the formation of coke on the catalyst particles.

The product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. The cyclic $C_5$ compounds comprise at least about 20 wt %, or 30 wt %, or 40 wt %, or 50 wt % cyclopentadiene, or in the range of from about 10 wt % to about 80 wt %, alternately 10 wt % to 80 wt % of cyclopentadiene.

The acyclic $C_5$ conversion conditions include at least a temperature, a partial pressure, and a weight hourly space velocity (WHSV). The temperature is in the range of about 450° C. to about 650° C., or in the range from about 500° C. to about 600° C., preferably, in the range from about 545° C. to about 595° C. The partial pressure is in the range of about 3 psia to about 100 psia (21 to 689 kPa-a), or in the range from about 3 psia to about 50 psia (21 to 345 kPa-a), preferably, in the range from about 3 psia to about 20 psia (21 to 138 kPa-a). The weight hourly space velocity is in the range from about 1 $hr^{-1}$ to about 50 $hr^{-1}$, or in the range from about 1 $hr^{-1}$ to about 20 $hr^{-1}$. Such conditions include a molar ratio of the optional hydrogen co-feed to the acyclic $C_5$ hydrocarbon in the range of about 0 to 3 (e.g., 0.01 to 3.0), or in the range from about 0.5 to about 2. Such conditions may also include co-feed $C_1$-$C_4$ hydrocarbons with the acyclic $C_5$ feed.

In any embodiments, this invention relates to a process for conversion of n-pentane to cyclopentadiene comprising the steps of contacting n-pentane and, optionally, hydrogen (if present, typically $H_2$ is present at a molar ratio of hydrogen to n-pentane of 0.01 to 3.0) with one or more catalyst compositions, including but not limited to the catalyst compositions described herein, to form cyclopentadiene at a temperature of 400° C. to 700° C., a partial pressure of 3 psia to about 100 psia (21 to 689 kPa-a), and a weight hourly space velocity of 1 $hr^{-1}$ to about 50 $hr^{-1}$.

In the presence of the catalyst, a number of desired and undesirable side reactions may take place. The net effect of the reactions is the production of hydrogen and the increase of total volume (assuming constant total pressure). One particularly desired overall reaction (i.e., intermediate reaction step that is not shown) is:

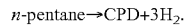
n-pentane→CPD+3$H_2$.

Additional overall reactions include, but are not limited to:

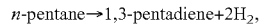
n-pentane→1,3-pentadiene+2$H_2$,

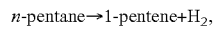
n-pentane→1-pentene+$H_2$,

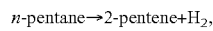
n-pentane→2-pentene+$H_2$,

n-pentane→2-methyl-2-butene+$H_2$,

n-pentane→cyclopentane+$H_2$,

cyclopentane→cyclopentene+$H_2$, or

cyclopentene→CPD+$H_2$.

Fluids inside the first reactor are essentially in gas phase. At the outlet of the first reactor, a first reactor hydrocarbon effluent, preferably in gas phase, is obtained. The first reactor hydrocarbon effluent may comprise a mixture of the following hydrocarbons, among others: heavy components comprising more than 8 carbon atoms such as multiple-ring aromatics; $C_8$, $C_7$, and $C_6$ hydrocarbons such as one-ring aromatics; CPD (the desired product); unreacted $C_5$ feedstock material such as n-pentane; $C_5$ by-products such as pentenes (1-pentene, 2-pentene, e.g.), pentadienes (1,3-pentadiene, 1,4-pentadiene, e.g.), cyclopentane, cyclopentene, 2-methylbutane, 2-methyl-1-butene, 3-methyl-1-butene, 2-methyl-1,3-butadiene, 2,2-dimethylpropane, and the like; $C_4$ by-products such as butane, 1-butene, 2-butene, 1,3-butadiene, 2-methylpropane, 2-methyl-1-propene, and the like; $C_3$ by-products such as propane, propene, and the like; $C_2$ by-products such as ethane and ethene, methane, and hydrogen.

The first reactor hydrocarbon effluent may comprise CPD at a concentration of C(CPD)1 wt %, based on the total weight of the $C_5$ hydrocarbons in the first reactor hydrocarbon effluent; and a1≤C(CPD)1≤a2, where a1 and a2 can be, independently, 15, 16, 18, 20, 22, 24, 25, 26, 28, 30, 32, 34, 35, 36, 38, 40, 45, 50, 55, 60, 65, 70, 75, 80, or 85 as long as a1<a2.

The first reactor hydrocarbon effluent may comprise acyclic diolefins at a total concentration of C(ADO)1 wt %, based on the total weight of the $C_5$ hydrocarbons in the first reactor hydrocarbon effluent; and b1≤C(ADO)1≤b2, where b1 and b2 can be, independently, 20, 18, 16, 15, 14, 12, 10, 8, 6, 5, 4, 3, 2, 1, or 0.5, as long as b1<b2. Preferably, 0.5≤C(ADO)≤10.

As a result of the use of the catalyst and the choice of reaction conditions in the first reactor, a high CPD to acyclic diolefin molar ratio in the first reactor hydrocarbon effluent can be achieved such that C(CPD)1/C(ADO)1≥1.5, preferably 1.6, 1.8, 2.0, 2.2, 2.4, 2.5, 2.6, 2.8, 3.0, 3.2, 3.4, 3.5, 3.6, 3.8, 4.0, 5.0, 6.0, 8.0, 10, 12, 14, 15, 16, 18, or 20. The high ratio of C(CPD)1/C(ADO)1 significantly reduces CPD loss as a result of Diels-Alder reactions between CPD and acyclic dienes in subsequent processing steps, and therefore, allows the processes of the present invention to achieve high DCPD yield and high DCPD purity for the subsequently produced DCPD fractions.

Desirably, the total absolute pressure and temperature of the first reactor hydrocarbon effluent should be maintained at levels such that the dimerization of CPD to form DCPD is substantially avoided, and the Diels-Alder reactions between CPD and acyclic dienes are substantially inhibited.

Because the overall conversion from acyclic $C_5$ hydrocarbons to CPD and hydrogen results in substantial volume increase (assuming constant total system pressure), a low partial pressure of CPD and/or a low partial pressure of hydrogen in the reaction mixture favors the conversion of acyclic $C_5$ hydrocarbons. The total partial pressure of $C_5$ hydrocarbons and hydrogen in the first reactor effluent at the outlet is desired to be lower than atmospheric pressure. Thus, where insufficient co-feedstock of a $C_1$-$C_4$ hydrocarbon or other co-feedstock is introduced into the first reactor, the total overall pressure of the first reactor effluent is desirably sub-atmospheric, in order to achieve a level of satisfactory conversion from acyclic $C_5$ hydrocarbons to CPD. However, direct separation of a sub-atmospheric stream has the disadvantage of potential oxygen/air ingress into the system, resulting in oxidation of CPD and other hydrocarbons and formation of undesirable species in the system. Thus, it is desirable that the first reactor hydrocarbon effluent is processed to a higher total pressure before separation thereof. Eductor systems, can be used for that purpose (as described in U.S. Ser. No. 62/250,708, filed Nov. 4, 2015).

Catalyst Composition

The second aspect of the invention is a catalyst composition for the conversion of an acyclic $C_5$ feedstock and, optionally, hydrogen to a product comprising cyclic $C_5$ compounds including cyclopentadiene. The catalyst composition comprises a microporous crystalline aluminosilicate having a constraint index of less than about 5, and a Group 10 metal in combination with a Group 1 alkali metal and/or a Group 2 alkaline earth metal and, optionally, a Group 11 metal.

Suitable aluminosilicates having a constraint index of less than or equal to 5 include, or and are selected from the group consisting of zeolite beta, mordenite, faujasite, zeolite L, and mixtures of two or more thereof. Preferably, the crystalline aluminosilicate that has a constraint index of less than or equal to 5 is zeolite L. Constraint index and a method for its determination are described in U.S. Pat. No. 4,016,218, referenced above.

Zeolite L may be synthesized in various crystal morphologies; the "hockey puck" morphology is preferred where the channel direction is parallel to the shorter axis of the crystal. See, U.S. Pat. No. 5,491,119. Zeolite L is described in U.S. Pat. No. 3,216,789. Zeolite beta is described in U.S. Pat. Nos. 3,308,069, and Reissue 28,341. Mordenite is a naturally occurring material, but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. Faujacite is a naturally occurring material but is also available in synthetic forms, such as zeolite Y, Ultrastable Y (USY), Dealuminized Y (Deal Y), Ultrahydrophobic Y (UHP-Y) and Rare earth exchanged Y (REY). Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Ultrahydrophobic Y (UHP-Y) is described in U.S. Pat. No. 4,401,556. Rare earth exchanged Y (REY) is described in U.S. Pat. No. 3,524,820. The entire contents of each of the aforementioned patents are incorporated herein by reference.

The microporous crystalline aluminosilicate has a $SiO_2/Al_2O_3$ molar ratio greater of at least about 2, or at least about 3, or preferably in the range of from about 2 up to about 20.

The crystalline aluminosilicate has a BET surface area of at least 275 $m^2/g$, or in the range of about greater than about 275 $m^2/g$ to less than about 400 $m^2/g$.

The Group 10 metal includes, or is selected from the group consisting of, nickel, palladium and platinum, preferably platinum. The Group 10 metal content of said catalyst composition is at least 0.005 wt %, based on the weight of the catalyst composition. Alternatively, the Group 10 content is in the range from about 0.005 wt % to about 10 wt %, or from about 0.005 wt % up to about 1.5 wt %, based on the weight of the catalyst composition.

The Group 1 alkali metal includes, or is selected from the group consisting of, lithium, sodium, potassium, rubidium, cesium, and mixtures of two or more thereof, preferably potassium.

The Group 2 alkaline earth metal includes, or is selected from the group consisting of beryllium, magnesium, calcium, strontium, barium, and mixtures of two or more thereof.

The molar ratio of the sum of said Group 1 alkali metal and said Group 2 alkaline earth metal to Al is at least about 0.5, or in the range from at least about 0.5 up to about 2, preferably at least about 1, more preferably at least about 1.5.

Alternatively, the Group 1 alkali metal and/or said Group 2 alkaline earth metal is present as an oxide. The Group 1 alkali metal oxide is an oxide of lithium, sodium, potassium, rubidium, cesium and mixtures of two or more thereof. The Group 2 alkaline earth metal oxide is an oxide of beryllium, magnesium, calcium, strontium, barium, and mixtures of two or more thereof.

The use of the catalyst compositions of this invention provides a conversion of at least about 10%, or at least about 20%, or at least about 30%, or in the range of from about 20% to about 50%, of said acyclic $C_5$ feedstock under acyclic $C_5$ conversion conditions of an n-pentane containing feedstock with equimolar $H_2$, a temperature in the range of from 400° C. to about 500° C., or about 450° C., an n-pentane partial pressure of about 5 psia (35 kPa-a), or about 7 psia (48 kPa-a), or from about 4 psia to about 6 psia at the reactor inlet (28 to 41 kPa-a), and an n-pentane weight hourly space velocity of about 2 $hr^{-1}$, or between 1 $hr^{-1}$ and 5 $hr^{-1}$.

The use of any one of the catalyst compositions of this invention provides a carbon selectivity to cyclic $C_5$ compounds of at least about 10%, or at least about 20%, or at least about 30%, or in the range from about 20% to about 50%, under acyclic $C_5$ conversion conditions including an n-pentane feedstock with equimolar $H_2$, a temperature in the range of about 400° C. to about 500° C., or about 450° C., an n-pentane partial pressure between 3 psia and 10 psia (21 to 69 kPa-a), and an n-pentane weight hourly space velocity between 10 $hr^{-1}$ and 20 $hr^{-1}$.

The use of any one of the catalyst compositions of this invention provides a carbon selectivity to cyclopentadiene of at least about 20%, or at least about 30%, or at least about 40%, or at least about 50%, or in the range from about 30% to about 50%, under acyclic $C_5$ conversion conditions including an n-pentane feedstock with equimolar $H_2$, a temperature in the range of about 550° C. to about 600° C., an n-pentane partial pressure of about 7 psia (48 kPa-a), or about 5 psia (35 kPa-a), or from about 4 psia to about 6 psia (28 to 41 kPa-a), and an n-pentane weight hourly space velocity of about 2 $hr^{-1}$, or between 1 $hr^{-1}$ and 5 $hr^{-1}$.

The catalyst compositions of this invention can be combined with a matrix or binder material to render them attrition resistant and more resistant to the severity of the conditions to which they will be exposed during use in hydrocarbon conversion applications. The combined compositions can contain 1 wt % to 99 wt % of the materials of the invention based on the combined weight of the matrix (binder) and material of the invention. The relative proportions of zeolite crystalline material and matrix may vary widely, with the crystal content ranging from about 1 wt % to about 90 wt % and more usually, particularly when the composite is prepared in the form of beads, in the range of about 2 wt % to about 80 wt % of the composite.

During the use of the catalyst compositions in the processes of this invention, coke may be deposited on the catalyst compositions, whereby such catalyst compositions lose a portion of its catalytic activity and become deactivated. The deactivated catalyst compositions may be regenerated by conventional techniques including high pressure hydrogen treatment and combustion of coke on the catalyst compositions with an oxygen-containing gas.

Method of Making the Catalyst Compositions

In the third aspect of the invention, the method of making the catalyst composition comprising the steps of:
(a) providing a crystalline aluminosilicate comprising a Group 1 alkali metal and/or a Group 2 alkaline earth metal and having a constraint index of less than or equal to 5;
(b) optionally, treating said crystalline aluminosilicate with an acid at a PH of greater than or equal to 7 to increase the surface area of said crystalline aluminosilicate and to form an acid-treated aluminosilicate; and
(c) contacting said acid-treated aluminosilicate of step (b) with a source of a Group 10 metal to form said catalyst composition, whereby said catalyst composition having said Group 10 metal, and/or, optionally, said Group 11 metal, deposited thereon.

The Group 10 metal may be added to the catalyst composition during or after synthesis of the crystalline molecular sieve as any suitable Group 10 metal compound.

One Group 10 metal is platinum, and a source of platinum includes, but is not limited to, one or more platinum salts, such as, for example, platinum nitrate, chloroplatinic acid, platinous chloride, platinum amine compounds, particularly, tetraamine platinum hydroxide, and mixtures of two or more thereof. Alternatively, a source of platinum is selected from the group consisting of chloroplatinic acid, platinous chloride, platinum amine compounds, particularly, tetraamine platinum hydroxide, and mixtures of two or more thereof.

The source of Group 11 metal is a source of copper or silver. The source of copper is selected from the group consisting of copper nitrate, copper nitrite, copper acetate, copper hydroxide, copper acetylacetonate, copper carbonate, copper lactate, copper sulfate, copper phosphate, copper chloride, and mixtures of two or more thereof. The source of silver is selected from the group consisting of silver nitrate, silver nitrite, silver acetate, silver hydroxide, silver acetylacetonate, silver carbonate, silver lactate, silver sulfate, silver phosphate, and mixtures of two or more thereof. When Group 10 and/or Group 11 metals are added post-synthesis, they may be added by incipient wetness, spray application, solution exchange, and chemical vapor disposition or by other means known in the art.

The amount deposited of said Group 10 metal and/or said Group 11 metal is at least 0.005 wt %, based on the weight of the catalyst composition, or in the range from 0.005 wt % to 10 wt %, based on the weight of the catalyst composition.

In the fourth aspect of the invention, the catalyst composition is made by the method of this invention.

INDUSTRIAL APPLICABILITY

The first hydrocarbon reactor effluent obtained during the acyclic $C_5$ conversion process containing cyclic, branched and linear $C_5$ hydrocarbons and, optionally, containing any combination of hydrogen, $C_4$ and lighter byproducts, or $C_6$ and heavier byproducts is a valuable product in and of itself. Preferably, CPD and/or DCPD may be separated from the reactor effluent to obtain purified product streams, which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

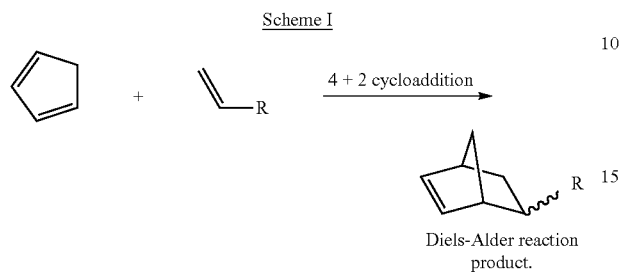

where R is a heteroatom or substituted heteroatom, substituted or unsubstituted $C_1$-$C_{50}$ hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the monoolefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins, and substituted versions of the foregoing. Preferred Diels-Alder reaction products include norbornene, ethylidene norbornene, substituted norbornenes (including oxygen-containing norbornenes), norbornadienes, and tetracyclododecene, as illustrated in the following structures:

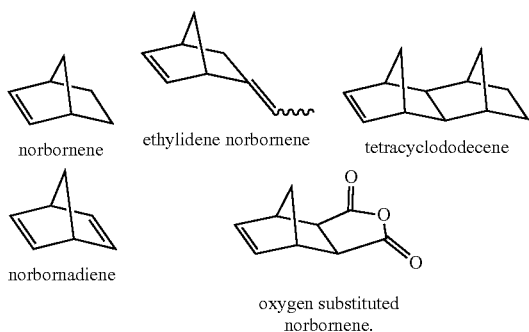

The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g. wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

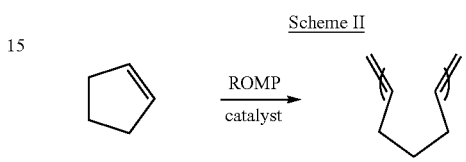

Separated cyclopentane is useful as a blowing agent and as a solvent. Linear and branched $C_5$ products are useful for conversion to higher olefins and alcohols. Cyclic and non-cyclic $C_5$ products, optionally, after hydrogenation, are useful as octane enhancers and transportation fuel blend components.

EXAMPLES

The following examples illustrate the present invention. Numerous modifications and variations are possible and it is to be understood that within the scope of the appended claims, the invention may be practiced otherwise than as specifically described herein.

Measurement of Total Surface Area by BET

The total BET was measured by nitrogen adsorption/desorption with a Micromeritics Tristar II 3020 instrument after degassing of the calcined zeolite powders for 4 hrs at 350° C. More information regarding the method can be found, for example, in "Characterization of Porous Solids and Powders: Surface Area, Pore Size and Density", S. Lowell et al., Springer, 2004.

X-ray Diffraction Patterns

The X-ray diffraction data (powder XRD or XRD) were collected with a Bruker D4 Endeavor diffraction system with a VANTEC multichannel detector using copper K-alpha radiation. The diffraction data were recorded by scanning mode with 0.018 degrees two-theta, where theta is the Bragg angle, and using an effective counting time of about 30 seconds for each step.

Example 1

Zeolite L Catalyst Composition Synthesis

A zeolite synthesis gel of composition, 3 $K_2O$:$Al_2O_3$:9 $SiO_2$:135 $H_2O$, was prepared by first making a potassium aluminate solution. To 1750 ml of distilled water was added 1450.3 g of KOH.½$H_2O$ (86.8% KOH) and 1166.7 g of $Al_2O_3$.3$H_2O$ (ALCOA C-31). The mixture was heated to a mild boil with stirring until alumina dissolved. The mixture was then allowed to cool down to room temperature. Final weight of mixture was 3991 g. An alum solution was prepared by dissolving 1820.1 g of $Al_2(SO_4)_3 \cdot 17H_2O$ in 2672 ml of distilled water. Twelve zeolite slurries were then prepared by slowly adding 1762 g of Kasil-6 potassium silicate (PQ Corp. 12.5% $K_2O$, 26.3% $SiO_2$), 332 g of potassium aluminate solution, 374 g of alum solution and 532 ml of distilled $H_2O$ to a 1 gallon Hobart mixer with stirring. The mixtures were then thoroughly homogenized in a laboratory blender and transferred to two 6 gallon HDPE plastic containers. The plastic containers were sealed and placed in a 100° C. oven for three days. The product was recovered by vacuum filtration, washed thoroughly with distilled water and then dried in an oven at 125° C. Analysis by powder X-ray diffraction showed the product to be pure zeolite L. Yield=6.0 Kg, Si/Al=2.65, K/Al=1.04, crystal size (SEM)=0.2-0.1 µm, BET surface area=291 $m^2/g$.

A portion of the acid washed zeolite L was pressed, crushed and sieved to 20/40 mesh. Then 98.3 g of dried sieved zeolite was added to a 28 cm column. A solution of 1.539 g of $Pt(NH_3)_4C_{12} \cdot H_2O$ and 0.783 g of KCl in 190 ml of deionized water was prepared and added to the column. The solution was circulated from the bottom to the top with a peristalic pump for 75 minutes. Initial pH=6.78, temperature=24.0° C. Final pH=8.31, temperature=27.0° C. The solution and zeolite was then aged for 3 days at 50° C. The sample was separated from the excess liquid and air dried 50° C. for 1 hr, 70° C. for 1 hr, 90° C. for 1 hr, and at 20° C./hr ramp. The sample was then calcined by placing in 100° C. furnace and then ramping to 200° C. for 2 hr, 350° C. in 3 hr with 500 cc/min air flow rate. Pt content was measured and determined to be 0.5 wt % of total catalyst weight.

Example 2

Catalyst Composition Performance Evaluation

The above material of Example 1 was evaluated for performance. The catalyst composition (0.25 g, 20-40 mesh) was physically mixed with quartz (6.5 g, 60-80 mesh) and loaded into a reactor. The catalyst composition was dried for 1 hour under $H_2$ (200 mL/min, 50 psia (345 kPa-a), 250° C.) then reduced for 5 hours under $H_2$ (200 mL/min, 50 psia (345 kPa-a), 500° C.). The catalyst composition was then tested for performance with feed of n-pentane, $H_2$, and balance Ar, typically at 451° C., 7.0 psia (48 kPa-a) $C_5H_{12}$, 1.0 molar $H_2:C_5H_{12}$, 1.9 $hr^{-1}$ and 19.9 $hr^{-1}$ WHSV, and 50 psia (345 kPa-a) total. Catalyst composition stability and regenerability was tested post initial tests by treating with $H_2$ at 650° C. (200 mL/min, 50 psia (345 kPa-a) for 5 hrs then retesting performance at 451° C.

Cyclopentadiene, and three equivalents of hydrogen, are produced by the conversion of n-pentane (Equation 1). This is achieved by flowing n-pentane over a solid-state, Pt containing catalyst composition at elevated temperature. The performance of ZSM-5(Si/Al=2.65Si)/0.5% Pt of Example 1 was evaluated based on n-pentane conversion, cyclic $C_5$ production ($cC_5$), cracking yields, and stability.

$$C_5H_{12} \xrightarrow{\Delta} C_5H_6 + 3H_2 \quad \text{Equation (1)}$$

TABLE 1A

| WHSV ($hr^{-1}$) | TOS (hr) | Temperature (° C.) | Conversion (%) $C_5H_{12}$ | Selectivity (mol %) | | | | Yield (mol %) | | | |
|---|---|---|---|---|---|---|---|---|---|---|---|
| | | | | $cC_5$ | CPD | $C_1$ | $C_{2-4}$ | $cC_5$ | CPD | $C_1$ | $C_{2-4}$ |
| 19.9 | 0.9 | 451 | 12.7 | 21.6 | 1.0 | 8.1 | 11.0 | 2.8 | 0.1 | 1.0 | 1.4 |
| 1.9 | 1.9 | 451 | 30.2 | 18.0 | 0.7 | 25.3 | 28.2 | 5.4 | 0.2 | 7.6 | 8.5 |
| 19.9 | 4.9 | 451 | 10.2 | 15.1 | 1.1 | 8.9 | 11.0 | 1.5 | 0.1 | 0.9 | 1.1 |
| 19.9 | 6.1 | 451, Post $H_2$ | 10.4 | 24.5 | 1.1 | 2.7 | 4.8 | 2.6 | 0.1 | 0.3 | 0.5 |
| 1.9 | 7.1 | 451, Post $H_2$ | 19.8 | 30.6 | 0.7 | 10.4 | 15.4 | 6.0 | 0.1 | 2.1 | 3.0 |
| 19.9 | 9.2 | 451, Post $H_2$ | 8.2 | 16.3 | 1.2 | 2.7 | 4.4 | 1.3 | 0.1 | 0.2 | 0.4 |

TABLE 1B

| WHSV ($hr^{-1}$) | TOS (hr) | Temperature (° C.) | Conversion (%) $C_5H_{12}$ | Selectivity (C %) | | | | Yield (C %) | | | |
|---|---|---|---|---|---|---|---|---|---|---|---|
| | | | | $cC_5$ | CPD | $C_1$ | $C_{2-4}$ | $cC_5$ | CPD | $C_1$ | $C_{2-4}$ |
| 19.9 | 0.9 | 451 | 12.7 | 29.0 | 1.3 | 2.2 | 9.1 | 3.7 | 0.2 | 0.3 | 1.2 |
| 1.9 | 1.9 | 451 | 30.2 | 30.9 | 1.3 | 8.7 | 29.3 | 9.3 | 0.4 | 2.6 | 8.8 |
| 19.9 | 4.9 | 451 | 10.2 | 19.0 | 1.3 | 2.2 | 8.4 | 1.9 | 0.1 | 0.2 | 0.9 |
| 19.9 | 6.1 | 451, Post $H_2$ | 10.4 | 31.2 | 1.4 | 0.7 | 3.7 | 3.3 | 0.1 | 0.1 | 0.4 |
| 1.9 | 7.1 | 451, Post $H_2$ | 19.8 | 48.2 | 1.1 | 3.3 | 14.8 | 9.5 | 0.2 | 0.6 | 2.9 |
| 19.9 | 9.2 | 451, Post $H_2$ | 8.2 | 18.7 | 1.4 | 0.6 | 3.1 | 1.5 | 0.1 | 0.1 | 0.3 |

Table 1A and Table 1B show the conversion of n-pentane and selectivity and yield of cyclic $C_5$, CPD, $C_1$, and $C_{2-4}$ cracking products at varying space velocities (average values at each space velocity).

In Table 1A, the selectivities and yields are expressed on a molar percentage basis for the respective cyclic $C_5$, CPD, $C_1$, and $C_{2-4}$ of hydrocarbons formed; i.e., the molar selectivity is the moles of the respective cyclic $C_5$, CPD, $C_1$, and $C_{2-4}$ formed divided by total moles of pentane converted. In Table 1B, the selectivities and yields are expressed on a carbon percentage basis for the respective cyclic $C_5$, CPD, $C_1$, and $C_{2-4}$ of hydrocarbons formed; i.e., the carbon selectivity is the moles carbon in the respective cyclic $C_5$, CPD, $C_1$, and $C_{2-4}$ formed divided by total moles of carbon in the pentane converted. The data sets in Table 1A correspond to those in Table 1B.

As can be seen, Table 1A and Table 1B show that near equilibrium yield of cyclic $C_5$ and CPD is possible at 1.9 WHSV. Some decline in cyclic yield is seen while on oil (data sets 1 vs. 3 and 4 vs. 6), but it is demonstrated that the 650° C. $H_2$ exposure can restore at least a portion of the cyclization activity (hypothesized to be due to removal of coke); the 650° C. $H_2$ exposure has the additional beneficial effect of reducing the selectivity to cracked products so that the thermodynamic constrained yield of cyclic products is increased. This performance is greatly superior to other dehydrogenation catalysts, such as aluminas and aluminates.

Certain embodiments and features have been described using a set of numerical upper limits and a set of numerical lower limits. It should be appreciated that ranges from any lower limit to any upper limit are contemplated unless otherwise indicated. Certain lower limits, upper limits, and ranges appear in one or more claims below. All numerical values take into account experimental error and variations that would be expected by a person having ordinary skill in the art.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition element, or elements and vice versa.

What is claimed is:

1. A process for conversion of an acyclic $C_5$ feedstock to a product comprising cyclic $C_5$ compounds including cyclopentadiene, said process comprising the steps of contacting said feedstock and, optionally, hydrogen under acyclic $C_5$ conversion conditions in the presence of a catalyst composition to form said product, wherein said catalyst composition comprises a microporous crystalline aluminosilicate having a constraint index of less than or equal to 5 selected from the group consisting of zeolite beta, mordenite, faujasite, zeolite L, and mixtures of two or more thereof, and a Group 10 metal in combination with a Group 1 alkali metal and/or a Group 2 alkaline earth metal and, optionally, a Group 11 metal.

2. The process of claim 1, wherein said catalyst composition has Group 10 metal content in the range from 0.005 wt % to 10 wt %, based on the weight of the catalyst composition.

3. The process of claim 1, wherein said Group 10 metal is platinum, and said Group 11 metal is copper or silver.

4. The process of claim 1, wherein said Group 1 alkali metal and/or said Group 2 alkaline earth metal is present as an oxide.

5. The process of claim 1, wherein said Group 1 alkali metal is selected from the group consisting of lithium, sodium, potassium, rubidium, cesium, and mixtures of two or more thereof.

6. The process of claim 1, wherein said Group 2 alkaline earth metal is selected from the group consisting of beryllium, magnesium, calcium, strontium, barium, and mixtures of two or more thereof.

7. The process of claim 1, wherein said crystalline aluminosilicate has a $SiO_2/Al_2O_3$ molar ratio of at least 2.

8. The process of claim 1, wherein said crystalline aluminosilicate has a BET surface area of at least 275 $m^2/g$.

9. The process of claim 1, wherein said crystalline aluminosilicate has a molar ratio of the sum of said Group 1 alkali metal, and said Group 2 alkaline earth metal to Al is at least 0.5.

10. The process of claim 1, wherein said catalyst composition provides a conversion of at least 20% of said acyclic $C_5$ feedstock under acyclic $C_5$ conversion conditions including an n-pentane feedstock with equimolar $H_2$, a temperature of 450° C., an n-pentane partial pressure of 7 psia at the reactor inlet (48 kPa-a), and an n-pentane weight hourly space velocity of 2 $hr^{-1}$.

11. The process of claim 1, wherein said catalyst composition provides a carbon selectivity to cyclic $C_5$ compounds of at least 20% under acyclic $C_5$ conversion conditions including an n-pentane feedstock with equimolar $H_2$, a temperature of 450° C., an n-pentane partial pressure of 7 psia at the reactor inlet (48 kPa-a), and an n-pentane weight hourly space velocity of 2 $hr^{-1}$.

12. The process of claim 1, wherein said acyclic $C_5$ feedstock comprises pentane, pentene, pentadiene, and mixtures of two or more thereof.

13. The process of claim 1, wherein said cyclic $C_5$ compounds comprise cyclopentane, cyclopentene, cyclopentadiene, and mixtures of two or more thereof.

14. The process of claim 1, wherein said acyclic $C_5$ feedstock comprises at least 75 wt % n-pentane.

15. The process of claim 1, wherein said cyclic $C_5$ compounds comprise at least 20 wt % cyclopentadiene.

16. The process of claim 1, wherein said acyclic $C_5$ conversion conditions include at least a temperature of 450° C. to 650° C., the molar ratio of said optional hydrogen co-feed to the acyclic $C_5$ feedstock is in the range of 0.01 to 3, said acyclic $C_5$ feedstock has a partial pressure in the range of 3 to 100 psia at the reactor inlet (21 to 689 kPa-a), and said acyclic $C_5$ feedstock has a weight hourly space velocity in the range from 0.5 to 50 $hr^{-1}$.

17. A process for conversion of an acyclic $C_5$ feedstock to a product comprising cyclic $C_5$ compounds including cyclopentadiene, said process comprising the steps of contacting said feedstock and, optionally, hydrogen under acyclic $C_5$ conversion conditions in the presence of a catalyst composition to form said product, wherein said catalyst composition is made by the method comprising the steps of:

(a) providing a crystalline aluminosilicate comprising a Group 1 alkali metal and/or a Group 2 alkaline earth metal and having a constraint index of less than or equal to 5 selected from the group consisting of zeolite beta, mordenite, faujasite, zeolite L, and mixtures of two or more thereof;

(b) optionally, treating said crystalline aluminosilicate with an acid at a PH of greater than or equal to 7 to increase the surface area of said crystalline aluminosilicate and to form an acid-treated aluminosilicate; and (c) contacting said acid-treated aluminosilicate of step (b) with a source of a Group 10 metal, and, optionally, a Group 11 metal, to form said catalyst composition, whereby said catalyst composition having said Group 10 metal, and/or, optionally, said Group 11 metal, deposited thereon.

18. The process of claim 17, wherein said Group 10 metal is platinum and said source of platinum is selected from the group consisting of platinum nitrate, chloroplatinic acid, platinous chloride, platinum amine compounds, platinum acetylacetonate, tetraamine platinum hydroxide, and mixtures of two or more thereof, and/or said Group 11 metal is copper and said source of copper is selected from the group consisting of copper nitrate, copper nitrite, copper acetate, copper hydroxide, copper acetylacetonate, copper carbonate, copper lactate, copper sulfate, copper phosphate, copper chloride, and mixtures of two or more thereof, and/or said Group 11 metal is silver and/or said source of silver is selected from the group consisting of silver nitrate, silver nitrite, silver acetate, silver hydroxide, silver acetylacetonate, silver carbonate, silver lactate, silver sulfate, silver phosphate, and mixtures of two or more thereof.

* * * * *